US011213374B2

(12) United States Patent
Lancelle et al.

(10) Patent No.: US 11,213,374 B2
(45) Date of Patent: Jan. 4, 2022

(54) RENDERING A DENTAL MODEL IN AN IMAGE

(71) Applicant: Ivoclar Vivadent AG, Schaan (LI)

(72) Inventors: Marcel Lancelle, Zürich (CH); Roland Mörzinger, Zürich (CH); Nicolas Degen, Erlenbach (CH); Gabor Sörös, Zürich (CH); Bartolovic Nemanja, Zürich (CH)

(73) Assignee: Ivoclar Vivadent AG, Schaan (LI)

( * ) Notice: Subject to any disclaimer, the term of this patent is extended or adjusted under 35 U.S.C. 154(b) by 34 days.

(21) Appl. No.: 16/279,185

(22) Filed: Feb. 19, 2019

(65) Prior Publication Data

US 2019/0254790 A1   Aug. 22, 2019

(30) Foreign Application Priority Data

Feb. 20, 2018 (EP) .................................... 18157574
Feb. 21, 2018 (EP) .................................... 18157809
Sep. 28, 2018 (EP) .................................... 18197645

(51) Int. Cl.
| | |
|---|---|
| *A61C 13/34* | (2006.01) |
| *A61C 7/00* | (2006.01) |
| *A61C 13/00* | (2006.01) |
| *G16H 50/50* | (2018.01) |
| *A61C 9/00* | (2006.01) |

(52) U.S. Cl.
CPC .............. *A61C 13/34* (2013.01); *A61C 7/002* (2013.01); *A61C 13/0004* (2013.01); *G16H 50/50* (2018.01); *A61C 9/0046* (2013.01)

(58) Field of Classification Search
None
See application file for complete search history.

(56) References Cited

U.S. PATENT DOCUMENTS 7,717,708 B2   5/2010   Sachdeva et al.
9,775,491 B2   10/2017  Clausen et al.
(Continued)

OTHER PUBLICATIONS

Qiao, Chen et al., "An Augmented Reality Based Teeth Shade Matching System," Key Laboratory of Photoelectronic Imaging Technology and System, Ministry of Education of China School of Optics and Electronics, Beijing Institute of Technology, Beijing, pp. 371-374, 2011.
(Continued)

*Primary Examiner* — Vikkram Bali
(74) *Attorney, Agent, or Firm* — Ann M. Knab; Thad McMurray

(57) ABSTRACT

Method for realistic visualization of a virtual dental model in a first image of a face comprising at least an inner mouth region of the face, the inner mouth region comprising teeth (31) and a mouth cavity background, the method comprising using an inpainting algorithm to compute, based on background pixels corresponding to the mouth cavity background (35), plausible background pixels for at least a part of tooth pixels of the first image, the tooth pixels corresponding to the teeth, and to replace at least a part of the tooth pixels by plausible background pixels, at least partially removing the teeth (31) from the first image; and visualizing the first image with the at least partially removed teeth (31'), wherein the first image is overlaid with a representation (21) of the dental model.

14 Claims, 3 Drawing Sheets

(56) References Cited

U.S. PATENT DOCUMENTS

| | | |
|---|---|---|
| 2007/0127844 A1* | 6/2007 | Watanabe .......... G06K 9/00315 |
| | | 382/276 |
| 2011/0212420 A1 | 9/2011 | Vuillemot |
| 2013/0060532 A1 | 3/2013 | Clausen et al. |
| 2013/0158958 A1 | 6/2013 | Methot |
| 2014/0022249 A1* | 1/2014 | Ye ........................... G06K 9/00 |
| | | 345/420 |
| 2015/0350517 A1 | 12/2015 | Duret |
| 2017/0319293 A1 | 11/2017 | Fisker |
| 2018/0168780 A1* | 6/2018 | Kopelman ............ G06T 19/006 |
| 2018/0168781 A1 | 6/2018 | Kopelman et al. |

OTHER PUBLICATIONS

Shivaranjani, S. et al., "A Survey on Inpainting Techniques," International Conference on Electrical, Electronics, and Optimization Techniques (ICEEOT), pp. 2934-2937, 2016.

\* cited by examiner

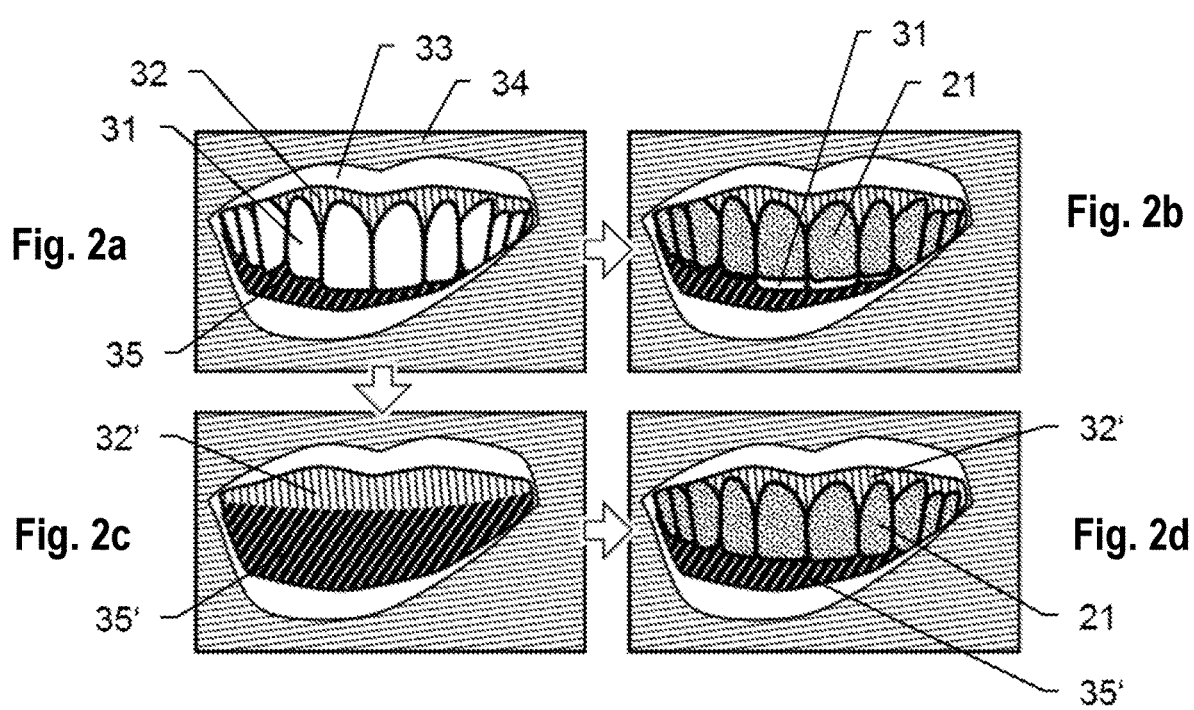

RENDERING A DENTAL MODEL IN AN IMAGE

CROSS-REFERENCE TO RELATED APPLICATIONS

This application claims priority to European patent application No. 18197645.7 filed on Sep. 28, 2018, European patent application No. 18157574.7 filed on Feb. 20, 2018, and European patent application No. 18157809.7 filed on Feb. 21, 2018, all the disclosures of which are incorporated herein by reference in their entirety.

TECHNICAL FIELD

The present invention pertains to a computer-implemented method for realistic visualization of virtual three-dimensional models of dentitions in an image or image stream of a person's face. In particular, the described method allows realistic visualization of dental models in dental virtual mock-up applications, such as dental augmented reality applications.

In the context of the present invention, the term "denture" is not necessarily restricted to full dentures but also comprises partial dentures, orthodontic situations or adaptations, or dental restorations such as dental prostheses, including crowns, crown lays, veneers, inlays and onlays, bridges, dental implants, and implant restorations. Accordingly, the term "dental model" includes all models of dental prostheses—such as models of complete and partial dentures—that are used for prosthodontic purposes.

For dentists and patients, it is of interest to get a visual impression of the appearance of the patient's face with a modified dental situation, i.e. to visualize the modified dental situation in an image of the face of the patient. Also, the appearance during or after a dental treatment may be of importance for the patient before deciding to undergo such treatment. For this purpose, a virtual preview (virtual mock-up) of the dentition modified by dental treatment is helpful for the dentist and may also be used in the course of interactively modifying the treatment plan to get the most favourable aesthetic results.

BACKGROUND

In dental virtual mock-up applications, virtual teeth are shown in a photo or video of a person's face or part thereof. Realistic visualization is important in this field, as humans are very sensitive to deviations from reality in human faces. This is a well-known problem called the "uncanny valley".

Overlaying a virtual dental model over an image of a face or mouth can lead to unsatisfying results when existing teeth are still visible in the image, e.g. because the existing teeth are larger than their virtual replacements.

U.S. Pat. No. 9,775,491 B2, which is hereby incorporated by reference in its entirety, discloses a computer implemented method for visualizing an image rendered from a three-dimensional model of a dental situation to an image of the face of the patient recorded by a camera. In this method a three-dimensional model of the oral cavity of the patient is obtained. This three-dimensional model is modified in a dentistry treatment plan by applying dental restorations to obtain a three-dimensional model of the dental situation of the patient dentition after application of the dental restorations. A two-dimensional image of the face of the patient including the mouth opening is obtained. Then the positioning of the camera that recorded the image relative to the dentition of the patient is estimated. In this application "positioning of the camera" meant to include the three-dimensional position x, y, z in space and the angular orientation of the camera with respect to the face of the patient. A virtual camera using the estimated positioning is processing the three-dimensional model of the dental situation to ob-taro a two-dimensional image, and a portion of the three-dimensional model of the dental situation is selected which is visible to the virtual camera. The image rendered by the virtual camera is overlaid and displayed in the image taken by the camera.

Similar methods are set forth in US 2011212420 directed to a method of forming a dental mold, US 20130060532 directed to a method of composing and designing teeth, US 2013158958 directed to a dental analysis method and system, US 20170319293 directed to a method of digitally designing a modified dental setup, and U.S. Pat. No. 7,717,708 directed to computer-based methods for supporting dentists during dental treatment planning for a patient, all of which are hereby incorporated by reference in their entirety.

SUMMARY

It is therefore an object of the present invention to provide an improved computer-implemented method that allows realistic visualization of a virtual three-dimensional dental model, e.g. a model of a full or partial denture, overlaid over an image of a face or mouth.

It is another object to provide such a method that allows overcoming or reducing the uncanny valley problem.

It is a further object to provide such a method wherein existing teeth in the image do not distract or disturb a user's perception of the visualized dental model.

It is another object to provide such a method that allows realistic rendering of the model in real-time, particularly in augmented-reality (AR) applications.

It is another object to provide such a method that can be performed on a mobile device with limited computing power.

It is another object to provide such a method that is performed fully or semi-automatically.

It is a further object to provide a handheld mobile device for performing such a method.

At least one of these objects is achieved by the method of claim 1, the mobile device of claim 14 and/or one of the dependent claims of the present application.

A first aspect of the invention pertains to a method for realistic visualization of a virtual dental model in a first image of a face, the first image showing at least an inner mouth region of the face, the inner mouth region comprising teeth and a mouth cavity background. The method comprises:

using an inpainting algorithm to compute, based on background pixels corresponding to the mouth cavity background, plausible background pixels for at least a part of tooth pixels of the first image, the tooth pixels corresponding to the teeth, and to replace at least a part of the tooth pixels by plausible background pixels, at least partially removing the teeth from the first image; and visualizing the first image with the at least partially removed teeth, wherein the first image is overlaid with a representation of the dental model.

In one embodiment, the mouth cavity background comprises at least a tongue and/or a palate. In another embodiment, the mouth cavity background also comprises gum.

According to one embodiment, the method comprises using a recognition algorithm to determine in the first image background pixels corresponding to the mouth cavity background and tooth pixels corresponding to the teeth.

According to another embodiment, the method comprises using a recognition algorithm to determine in a previously captured image of the same face background pixels corresponding to the mouth cavity background. In particular, in the previously captured image more of the mouth cavity background is visible than in the first image. For instance, the first image and the previously captured image can be part of the same image stream.

In one embodiment, the recognition algorithm is also used to determine in the first image tooth pixels corresponding to the teeth.

According to one embodiment of the method, computing the plausible background pixels comprises a stretching of a texture of the mouth cavity background along a vertical direction of the face in image space. The vertical direction e. g. can be defined by a direction of nose to chin or—vice versa—of chin to nose.

According to one embodiment, a three-dimensional proxy geometry is used for the stretching of the texture of the mouth cavity background, wherein the proxy geometry at least roughly follows an arch form slightly extending beyond the teeth.

According to another embodiment, a fragment shader, for instance using a texel lookup downwards with a weighted vector length, is used for the stretching of the texture of the mouth cavity background.

According to yet another embodiment, a distance in the image between teeth of the lower jaw and the upper jaw is determined, wherein the stretching of the texture of the mouth cavity background is performed only if the distance lies above a predetermined threshold.

According to a further embodiment, a necessary stretching degree is determined, the necessary stretching degree being that intensity of stretching of the texture of the mouth cavity background that is necessary to replace all tooth pixels that would be visible when the image is overlaid with the dental model, and the texture of the mouth cavity background is stretched at least with the determined necessary stretching degree, in particular exactly with the determined necessary stretching degree.

According to one embodiment of the method, the virtual dental model is an upper jaw dental model, wherein the method is performed only for the upper jaw, only tooth pixels corresponding to the teeth of the upper jaw being determined and replaced.

According to another embodiment of the method, the virtual dental model is a lower jaw dental model, wherein the method is performed only for the lower jaw, only tooth pixels corresponding to the teeth of the lower jaw being determined and replaced.

According to yet another embodiment of the method, the virtual dental model comprises an upper jaw dental model and a lower jaw dental model, wherein the determining and replacing tooth pixels corresponding to the teeth of the upper jaw and determining and replacing tooth pixels corresponding to the teeth of the lower jaw are performed subsequently.

According to another embodiment, the method comprises determining, before using the inpainting algorithm, whether tooth pixels are visible when the image is overlaid with the dental model. In particular, e. g. if the virtual dental model is an upper jaw dental model or a lower jaw dental model, the visibility is determined only for those tooth pixels that correspond to teeth of a jaw at which teeth of the virtual dental model are positioned.

According to another embodiment of the method, the first image is part of an image stream, and the method is performed in real time for at least a multitude of images of the image stream.

In one embodiment the method further comprises capturing the image stream by means of a camera and visualizing the dental model and the two-dimensional image on a displaying device to a user, particularly wherein the face is the face of the user.

If the camera and the displaying device are part of the same mobile device, according to one embodiment, the method is performed by means of one or more algorithms installed on a computing unit of said mobile device.

According to another embodiment of the method, the virtual dental model is in a polygon mesh format and comprises a plurality of vertices.

A second aspect of the invention pertains to a mobile device comprising a camera and a display that are arranged so that images of a user's face are capturable by the camera while the user watches the display—e. g. comprising a so-called selfie camera. The device comprises a computing unit with at least one algorithm that is adapted to perform the method according to the first aspect.

A further aspect of the invention pertains to a computer programme product comprising programme code which is stored on a machine-readable medium, or being embodied by an electromagnetic wave comprising a programme code segment, and having computer-executable instructions for performing the method according to the first aspect, in particular when executed on the computing unit of the mobile device according to the second aspect.

BRIEF DESCRIPTION OF THE DRAWINGS

The invention in the following will be described in detail by referring to exemplary embodiments that are accompanied by figures, in which:

FIGS. 2a-d illustrate a first exemplary embodiment of a method according to the invention.

DETAILED DESCRIPTION

Figure 1:
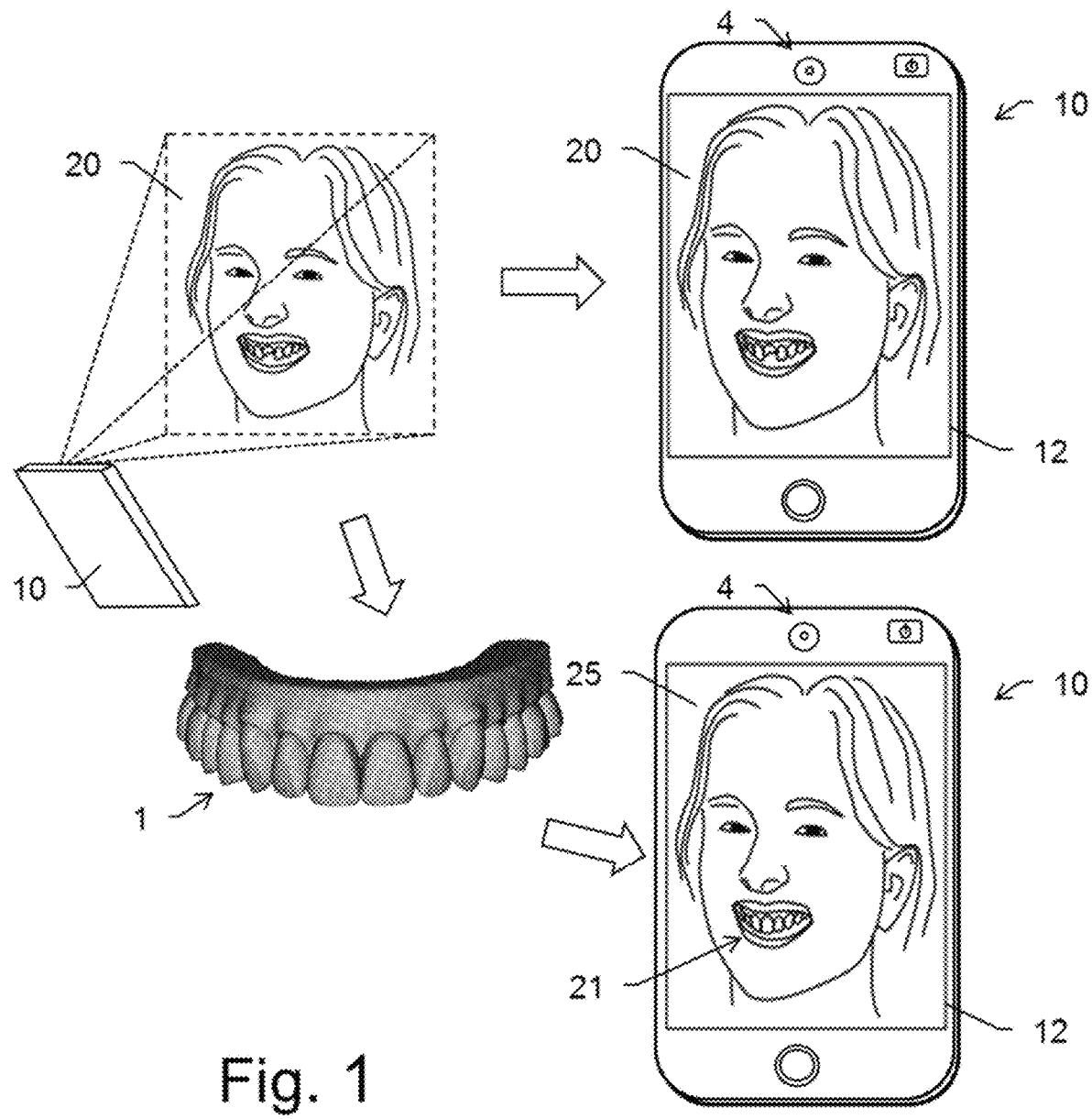
FIG. 1 illustrates an exemplary embodiment of a computer-implemented method for realistic visualization of a 3D dentition model in an image of a person's face.

FIG. 1 illustrates a computer-implemented method for realistic visualization of a 3D dentition model in an image of a person's face according to an exemplary embodiment of the invention.

According to the shown embodiment, an image 20 of the person's face is captured by means of a camera 4. In this embodiment, the camera 4 is part of a handheld mobile device 10 such as a smartphone. The device 10 comprises a display 12 which is enabled to display the image 20 in real time to the user, i.e. the patient whose image is captured. Data of a three-dimensional (3D) virtual dentition model 1 is provided in a data storage of the mobile device 10. An algorithm being provided in a computing unit of the mobile device 10 is adapted to fit the dentition model 1 into the image to provide an augmented-reality (AR) image 25 on the display 12, wherein the rendered dentition model 21 is displayed in the inner mouth region of the face. The processing can be performed offline on an image or video or in real time on a live camera image, thus providing a live augmented-reality application.

Humans are very sensitive to even slight deviations from reality in human faces. To overcome this "uncanny valley" problem in a visualization of virtual teeth in a photo or video of a face, realistic visualization of the 3D rendered content is crucial.

FIGS. 2*a-d* show four images of a mouth region of a person, e. g. of the face on the image of FIG. 1. FIG. 2*a* shows the original mouth region comprising the original teeth 31 of the upper jaw, the gum (or gingiva) 32, lips 33 and surrounding facial tissue 34. FIG. 2*a* also shows a mouth cavity background 35, i.e. the portion of the mouth cavity lying behind the teeth 31, comprising tongue and palate of the person.

FIG. 2*b* shows a 2D representation of a virtual 3D denture model 21 being overlaid over the image. As the teeth of the denture 21 are shorter than the original teeth 31, the latter are still visible in the image, which leads to unsatisfactory results. On the one hand, it is difficult to determine how a real denture produced according to the virtual denture 21 would look without the existing teeth. On the other hand, the "uncanny valley" effect may occur, leading to a psychologically motivated rejection of an otherwise perfect dental model.

FIGS. 2*c* and 2*d* illustrate a first exemplary embodiment of a method according to the invention. Pixels belonging to original teeth 31 of FIG. 2*a* are identified and replaced by pixels that form a plausible background of these teeth 31. The intermediate result is shown in FIG. 2*c*, where the teeth have been replaced by pixels that appear to be gum and background, the image thus showing an extended gum 32' and an extended mouth cavity background 35'. In FIG. 2*d*, the virtual denture representation 21 is overlaid over the image.

The method may comprise identifying the boundaries of the inner mouth region in the imaged face. The inner mouth region may comprise that part of the imaged face that lies inside the lips 33. The inner mouth region can either be defined by the user, e. g. by selecting the area in the image 20, or be automatically identified by means of a feature recognition algorithm.

Figure 3A:
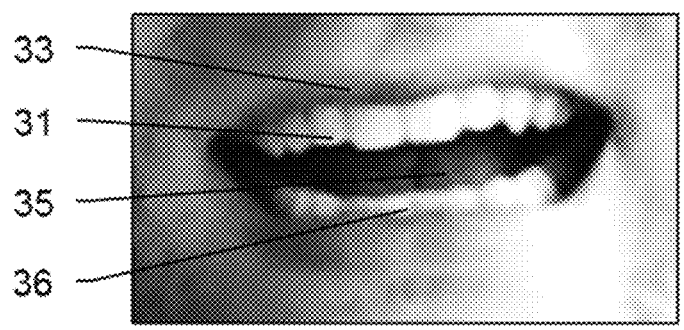
FIGS. 3a-c illustrate a second exemplary embodiment of a method according to the invention.
Figure 3B:
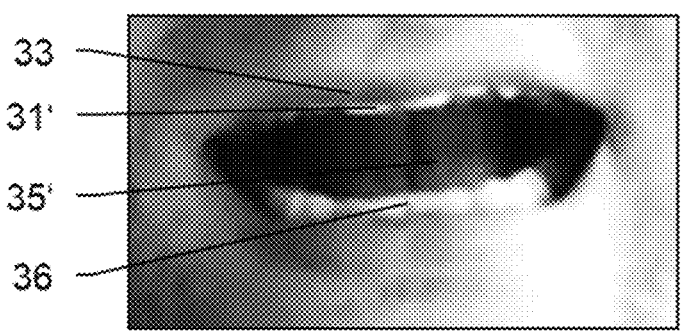
Figure 3C:

FIGS. 3*a-c* illustrate a second exemplary embodiment of a method according to the invention. In this embodiment, teeth 31 of an upper jaw are to be replaced by a denture, whereas the teeth 36 of the lower jaw will not be replaced. Accordingly, a virtual dental model for the upper jaw is provided, a 2D representation 21 of which needs to be overlaid over the image of the mouth.

FIG. 3*a* shows the original image of the mouth with the original teeth 31 of the upper jaw, lips 33, a mouth cavity background 35 comprising the tongue, and also teeth 36 of the lower jaw. The original teeth 31 are longer than those of the model and need to be shortened, i.e. partially replaced by plausible content, in order to not disturb the visualization. The lips 33 and lower teeth 36 should not be amended.

A recognition algorithm is used to determine in the image tooth pixels corresponding to the teeth 31 of the upper jaw and background pixels corresponding to the mouth cavity background 35. Afterwards, an inpainting algorithm is used to compute, based on the determined background pixels, plausible background pixels for at least a part of the tooth pixels, and to replace at least a part of the tooth pixels by plausible background pixels, i.e. at least partially removing the teeth 31 from the image.

In the embodiment presented here, computing the plausible background pixels comprises a stretching of existing texture of the mouth, such as the mouth cavity background 35. For doing so, a 3D proxy geometry can be used that roughly follows the arch form of the upper jaw and slightly extends beyond the teeth 31 of the upper jaw. A fragment shader can then be used to stretch the mouth cavity background 35. The stretching direction preferably is along the vertical direction of the face in image space. This is done by a texel lookup downwards (e. g. based on a direction of nose to chin) with a weighted vector length.

Optionally, a distance between the teeth 31 of the upper jaw and the teeth 36 of the lower jaw in the image can be determined, i.e. if the teeth were closed the distance would be zero. With a certain threshold of open teeth, the stretching is applied gradually.

If tooth pixels of the lower jaw would be hit, the lookup vector can be shortened iteratively to try to find another suitable pixel colour.

FIG. 3*b* shows as an intermediate result the inpainted image with shortened, i.e. partially removed, teeth 31' and stretched mouth cavity background 35'. Having partially removed the original teeth 31, the dental model can be overlaid. FIG. 3*c* shows the inpainted image of FIG. 3*b*, wherein the virtual teeth 21 are overlaid so that only the virtual teeth are visible, although these are shorter than the real teeth 31 of FIG. 3*a*, resulting in a realistic visualization of the dental model in the image.

Although the method is described only for the upper jaw it can likewise be applied to the lower jaw or both jaws.

In one embodiment, for computing the background pixels the same image that is to be visualized is used. In this case, advantageously, no further images need to be captured.

However, sometimes not enough of a mouth cavity background is visible in this image to create a realistic background for the removed tooth pixels.

Therefore, in another embodiment, the background pixels of another image of the same face can be used. In particular, this image has been captured previously. In this case, advantageously, an image can be used, wherein the mouth is opened wider so that more of the background is visible. This facilitates deleting the teeth in the visualized image. For instance, if sufficient mouth cavity background is visible no or less stretching needs to be applied to the mouth cavity background of the previously captured image to replace the tooth pixels in the visualized image. It is further not necessary to determine background pixels and tooth pixels in the visualized image, as it could be sufficient to determine the boundaries of the inner mouth region (e. g. that part of the imaged face that lies inside the lips) and replace the complete inner mouth region (i.e. teeth and background) of the visualized image with plausible background pixels from the previously captured image. Optionally, it can be determined whether the visible mouth cavity background in the first image (i.e. the visualized image) is sufficient for creating the plausible background. If it is not sufficient, a previous image or a number of previously captured images, e. g. from an image stream, can be checked with respect to their sufficiency of visible mouth cavity background. Alternatively, i.e. if there are no previous images or the mouth cavity background also in these images is not sufficient, the imaged patient can be prompted to open the mouth to allow capturing an image with sufficient visible mouth cavity background. In particular, this request can be displayed on a display in real time, e. g. on the display 12 of the handheld mobile device 10 of FIG. 1.

In an exemplary embodiment, a method for realistic visualization of a virtual dental model superimposed in a first image of a face is provided. The first image of the face includes at least a portion of an inner mouth region having teeth and a mouth cavity background. The method includes obtaining a virtual dental model. The dental model comprises a three-dimensional representation of a denture, implant(s), veneer(s), or other dental prosthesis. The method includes identifying a background region of the first image corresponding to the mouth cavity background and a tooth region corresponding to the teeth. A processor is used to compute plausible background pixels for at least a portion of the tooth region based on the background region. A revised image is generated using the processor, where the revised image is based on the first image having at least the portion of the tooth region replaced with the plausible background pixels. In this way, the teeth are at least partially removed from the revised image. A display is used to display a rendering of the dental model superimposed within the mouth cavity of the revised image.

In the context of the present invention, the term "denture" is not necessarily restricted to full dentures but also comprises partial dentures or orthodontic situation/adaptations or dental restorations such as dental prostheses, including crowns, crown lays, veneers, inlays and onlays, bridges, dental implants, implant restorations. Accordingly, the term "dental model" includes all models of dental prostheses as well as the patient situation that could be partial or fully edentulous—such as models of complete and partial dentures—that are used for prosthodontic purposes.

In some embodiments, the present disclosure is implemented using a system having a camera, a processor, an electronic data storage unit, and a display. The camera can be a standard camera, an infrared dot-projection detector, flood illuminator camera, structured-light three-dimensional scanner, standard infrared detector, ultrasonic imaging device, Doppler detector, or any other suitable visualization system capable of capturing information related to a patient's dentition. The processor can be a single processor having one or more cores, or a plurality of processors connected by a bus, network, or other data link. The electronic data storage unit can be any form of non-transitory computer-readable storage medium suitable for storing the data produced by the system. The display can be any display suitable for displaying a digital color or grayscale image.

In some embodiments, the camera, processor, electronic data storage unit, and digital display are components of a single device. The single device may be a smartphone, tablet, laptop computer, personal digital assistant, or other computing device.

In some embodiments, the processor is in communication over a network, which could be wired or wireless, with an external processor used for performing one or more calculation steps and/or a network-attached electronic data storage unit. In some embodiments, the present disclosure makes use of cloud computing to perform one or more calculations steps remotely and/or remote storage to enable the storage of data remotely for collaborative or remote analysis. In some embodiments, the system comprises a plurality of graphical user interfaces to permit multiple users to view or analyze the same data.

In some embodiments, the system operates to provide one or more users with a visualization of a virtual dental model of a patient's teeth, which may be altered to visualize the effect of one or more dental or orthodontic alterations. In some embodiments, this allows the one or more users to visualize a "before" dentition image, i.e., the appearance of a patient's dentition prior to a dental or orthodontic procedure, and an "after" dentition image, i.e., a representation of the expected appearance of a patient's dentition after a proposed dental or orthodontic procedure.

In some embodiments, the system operates by capturing information related to a patient's dentition using a camera, creating a model of the patient's dentition on a processor, fitting a model of a proposed post-alteration dentition to the patient's dentition on the processor, coloring the model of the proposed post-alteration dentition to match an expected real post-alteration coloration, and displaying the fitted model of the proposed post-alteration dentition in place of the patient's actual dentition on a display which otherwise shows the patient's actual facial features. The information related to a patient's dentition, the model of the patient's dentition, and the model of the proposed post-alteration dentition may be stored on an electronic data storage unit. In some embodiments, the operations are performed in real-time.

In some embodiments, a user interface is configured such that a user may view the "before" dentition image and the "after" dentition image simultaneously either side-by-side or with a full or partial overlay.

Where used herein, the term "non-transitory" is a limitation on the computer-readable storage medium itself—that is, it is tangible and not a signal—as opposed to a limitation on the persistence of data storage. A non-transitory computer-readable storage medium does not necessarily store information permanently. Random access memory (which may be volatile, non-volatile, dynamic, static, etc.), read-only memory, flash memory, memory caches, or any other tangible, computer-readable storage medium, whether synchronous or asynchronous, embodies it.

Although the invention is illustrated above, partly with reference to some preferred embodiments, it must be understood that numerous modifications and combinations of different features of the embodiments can be made. All of these modifications lie within the scope of the appended claims.

The invention claimed is:

1. A method for realistic visualization of a virtual dental model (1) in a first image (20) of a face comprising at least an inner mouth region of the face, the inner mouth region comprising teeth (31) and a mouth cavity background (35), the method comprising:
   using an inpainting algorithm
      to compute, based on background pixels corresponding to the mouth cavity background (35), plausible background pixels for at least a part of tooth pixels of the first image (20), the tooth pixels corresponding to the teeth (31), and
      to replace at least a part of the tooth pixels by plausible background pixels, at least partially removing the teeth (31) from the first image (20); and
   visualizing the first image (20) with the at least partially removed teeth (31'), wherein the first image (20) is overlaid with a representation (21) of the dental model (1),
wherein a recognition algorithm is used to determine in a previously captured image of the same face background pixels corresponding to the mouth cavity background (35), in particular wherein more of the mouth cavity background (35) is visible in the previously captured image than in the first image (20), particularly wherein the mouth cavity background (35) comprises at least a tongue and/or a palate.

2. The method according to claim 1,
characterized by
using the recognition algorithm to determine in the first image (20) and tooth pixels corresponding to the teeth (31).

3. The method according to claim 1,
characterized in that
the virtual dental model (1)
- is an upper jaw dental model, wherein the method is performed only for the upper jaw, only tooth pixels corresponding to the teeth (31) of the upper jaw being determined and replaced; or
- is a lower jaw dental model, wherein the method is performed only for the lower jaw, only tooth pixels corresponding to the teeth (31) of the lower jaw being determined and replaced; or
- comprises an upper jaw dental model and a lower jaw dental model, wherein the determining and replacing tooth pixels corresponding to the teeth (31) of the upper jaw and determining and replacing tooth pixels corresponding to the teeth (31) of the lower jaw are performed subsequently.

4. The method according to claim 1,
characterized in that
the image (20) is part of an image stream, and the method is performed in real time for at least a multitude of images (20) of the image stream.

5. Method according to claim 4,
characterized in that
the method further comprises capturing the image stream by means of a camera (4) and visualizing the dental model (1) and the two-dimensional image (20) on a displaying device (12) to a user, particularly wherein the face is the face of the user,
in particular wherein the camera (4) and the displaying device (12) are part of the same mobile device (10), wherein the method is performed by means of one or more algorithms installed on a computing unit of the mobile device (10).

6. The method according to claim 1,
characterized in that
the virtual dental model (1) is in a polygon mesh format and comprises a plurality of vertices.

7. A mobile device (10) comprising a camera (4) and a display (12) that arranged so that images (20) of a user's face are capturable by the camera (4) while the user watches the display (12),
characterized in that
the device comprises a computing unit with at least one algorithm that is adapted to perform the method of claim 1.

8. A computer programme product comprising programme code which is stored on a non-transitory machine-readable medium, the machine-readable medium comprising computer instructions executable by a processor, which computer instructions cause the processor to perform the method according to claim 1.

9. The computer programme product according to claim 8 executed on a mobile device comprising a camera (4) and a display (12) that is arranged so that images (20) of a user's face are capturable by the camera (4) while the user watches the display (12).

10. A method for realistic visualization of a virtual dental model (1) in a first image (20) of a face comprising at least an inner mouth region of the face, the inner mouth region comprising teeth (31) and a mouth cavity background (35), the method comprising:
using an inpainting algorithm
  to compute, based on background pixels corresponding to the mouth cavity background (35), plausible background pixels for at least a part of tooth pixels of the first image (20), the tooth pixels corresponding to the teeth (31), and
  to replace at least a part of the tooth pixels by plausible background pixels, at least partially removing the teeth (31) from the first image (20); and
visualizing the first image (20) with the at least partially removed teeth (31'), wherein the first image (20) is overlaid with a representation (21) of the dental model (1),
wherein computing the plausible background pixels comprises a stretching of a texture of the mouth cavity background (35) along a vertical direction of the face in image space, particularly wherein the vertical direction is a direction of nose to chin or a direction of chin to nose.

11. The method according to claim 10,
characterized in that
a three-dimensional proxy geometry is used for the stretching of the texture of the mouth cavity background (35), wherein the proxy geometry at least roughly follows an arch form slightly extending beyond the teeth (31); and/or
a fragment shader, particularly using a texel lookup downwards with a weighted vector length, is used for the stretching of the texture of the mouth cavity background (35).

12. The method according to claim 10,
characterized in that
a distance in the image (20) between teeth (31) of the lower jaw and the upper jaw is determined, wherein the stretching of the texture of the mouth cavity background (35) is performed only if the distance lies above a predetermined threshold.

13. The method according to claim 10,
characterized in that
a necessary stretching degree is determined, the necessary stretching degree being that intensity of stretching of the texture of the mouth cavity background (35) that is necessary to replace all tooth pixels that would be visible when the image (20) is overlaid with the dental model (1); and
the texture of the mouth cavity background (35) is stretched at least with the determined necessary stretching degree, in particular exactly with the determined necessary stretching degree.

14. A method for realistic visualization of a virtual dental model (1) in a first image (20) of a face comprising at least an inner mouth region of the face, the inner mouth region comprising teeth (31) and a mouth cavity background (35), the method comprising:
using an inpainting algorithm
  to compute, based on background pixels corresponding to the mouth cavity background (35), plausible background pixels for at least a part of tooth pixels of the first image (20), the tooth pixels corresponding to the teeth (31), and
  to replace at least a part of the tooth pixels by plausible background pixels, at least partially removing the teeth (31) from the first image (20); and
visualizing the first image (20) with the at least partially removed teeth (31'), wherein the first image (20) is overlaid with a representation (21) of the dental model (1), wherein, before using the inpainting algorithm, it is determined whether tooth pixels are visible when the image (20) is overlaid with the dental model (1),
    particularly wherein the visibility is determined only for those tooth pixels that correspond to teeth (31) of a jaw at which teeth of the virtual dental model (1) are positioned.

* * * * *